United States Patent [19]
Etter et al.

[11] Patent Number: 5,351,535
[45] Date of Patent: Oct. 4, 1994

[54] MECHANISM FOR INSERTING A THREAD INTO A YARN TESTER

[75] Inventors: Heinz Etter, Winterthur; Willi Schlaepfer, Fehraltorf, both of Switzerland

[73] Assignee: Zellweger Uster AG, Uster, Switzerland

[21] Appl. No.: 90,009

[22] Filed: Jul. 12, 1993

[51] Int. Cl.$^5$ .................. G01N 1/02; G01N 1/04; G01N 3/08; G01L 5/04
[52] U.S. Cl. ........................... 73/160; 226/92
[58] Field of Search ............... 73/160, 826; 226/92

[56] References Cited

U.S. PATENT DOCUMENTS

| | | | |
|---|---|---|---|
| 1,358,793 | 11/1920 | Smith | 226/92 |
| 2,590,398 | 3/1952 | Gegenschatz | 73/160 |
| 3,741,050 | 6/1973 | Coats et al. | 226/92 |
| 3,751,981 | 8/1973 | Jernigan et al. | 73/160 |
| 3,805,607 | 4/1974 | Heusser | 73/160 |
| 3,822,539 | 7/1974 | Heap et al. | 226/92 |
| 4,169,551 | 10/1979 | Jensen | 226/92 |
| 4,319,493 | 3/1982 | Roos | 73/828 |
| 4,560,098 | 12/1985 | Tupper | 226/92 |
| 5,050,437 | 9/1991 | Etter | 73/830 |
| 5,203,206 | 4/1993 | Shofner et al. | 73/160 |

FOREIGN PATENT DOCUMENTS 1306808 2/1973 United Kingdom ............... 226/92

Primary Examiner—Diego F. F. Gutierrez
Attorney, Agent, or Firm—Burns, Doane, Swecker & Mathis

[57] ABSTRACT

The insertion of thread into a yarn tester is accomplished by a mechanism that includes a clamp (3) for the thread end and an insertion arm (14) mounted for pivoting movement about a fixed axis to contact a portion of the thread above the clamp and swing a loop portion of the thread down into the space between feed rollers and to present the loop to a take-over nozzle (13). The thread is transferred from the insertion arm to the nozzle (13) and is fixed until transfer in the clamp (3), so that the thread transfer takes place in the form of a loop. Consequently, the insertion arm (14) need have no special thread clamp and can be of correspondingly simple design. The pivoting movement of the insertion arm (14) requires only a simple drive, and the take-over of the loop-shaped thread (F) by the take-over member is carried out without difficulty.

16 Claims, 3 Drawing Sheets

MECHANISM FOR INSERTING A THREAD INTO A YARN TESTER

FIELD OF THE INVENTION

The present invention relates to a mechanism for inserting a thread into a yarn tester which has a test stage and a take-over member for the inserted thread. It is concerned particularly with a mechanism in which an insertion arm and a clamp cooperate for feeding the thread to the take-over member of a tester.

BACKGROUND

A tearing-strength test apparatus known as the USTER TENSO JET (USTER being a registered trademark of Zellweger Uster AG) provides an example of a type of yarn tester which is of interest. This is described in EP-A-403,988 and its U.S. counterpart Pat. No. 5,050,437. In such a tester the stretching of the test material is carried out by two rotating pairs of rollers which are spaced from one another and between the rollers of which is formed a periodically opening and closing nip for the test material. This test apparatus is characterized by, among other things, a very high testing speed which, particularly in the testing of yarn from different bobbins, requires a corresponding insertion mechanism for the threads to be tested.

The cited EP-A-403,988 and its U.S. counterpart Pat. No. 5,050,437 mention and illustrate as a suitable insertion mechanism the mechanism which is known from the USTER TENSORAPID and which contains an insertion arm for the thread. This insertion arm is described in principle in U.S. Pat. No. 4,319,493. It is mounted in a link which is guided in a rail oriented vertically in the thread running direction, so that, during each insertion cycle, the head of the arm follows a path along a closed, approximately rectangular curve. The arm carries on its head a controlled thread clamp which grasps the thread, inserts it into the test apparatus and releases it after it has been taken over by the latter.

Practical tests have shown that this insertion mechanism works relatively slowly and the testing speed is consequently limited. The arm follows a relatively complicated path during the insertion of the thread, and during each insertion cycle, the thread clamp arranged on the arm has to be activated twice. Moreover, the transfer of the thread, drawn out by the insertion arm at its head part, to the take-over member is also relatively complicated and necessitates an exact positioning and synchronization between the take-over member and the thread clamp of the insertion arm. This known insertion mechanism also takes up a relatively large amount of space, giving rise not only to a cumbersome appearance but also to excess costs.

OBJECT AND SUMMARY OF THE INVENTION

An object of the invention is to provide an insertion mechanism which allows a high insertion frequency and as simple a thread transfer at the take-over member as is possible and which is characterized by a low space requirement.

According to the invention, an end of the thread is fixed in a clamp until an insertion arm has presented a loop portion of the thread to the take-over member. The insertion arm is designed as a pivoting arm mounted at a fixed location.

The mounting of the insertion arm at a fixed location and its design as a pivoting arm means that the thread fed to the insertion arm is drawn out in a simple pivoting movement and supplied to the take-over member. The looped draw-out means that there is no need for a thread clamp on the insertion arm itself, so that the latter can be of very simple design. The transfer of the loop-shaped thread to the take-over member likewise necessitates only a low outlay. If the take-over member is designed, for example, as an air nozzle, preferably as a suction nozzle, it is sufficient to position the thread transversely to the entry orifice of the latter, this being very simple with a thread loop. The insertion mechanism according to the invention also has a low space requirement.

BRIEF DESCRIPTION OF THE DRAWINGS

The invention is explained in more detail below with reference to an exemplary embodiment and the accompanying drawings; in which.

DETAILED DESCRIPTION OF PREFERRED EMBODIMENTS

Figure 1:
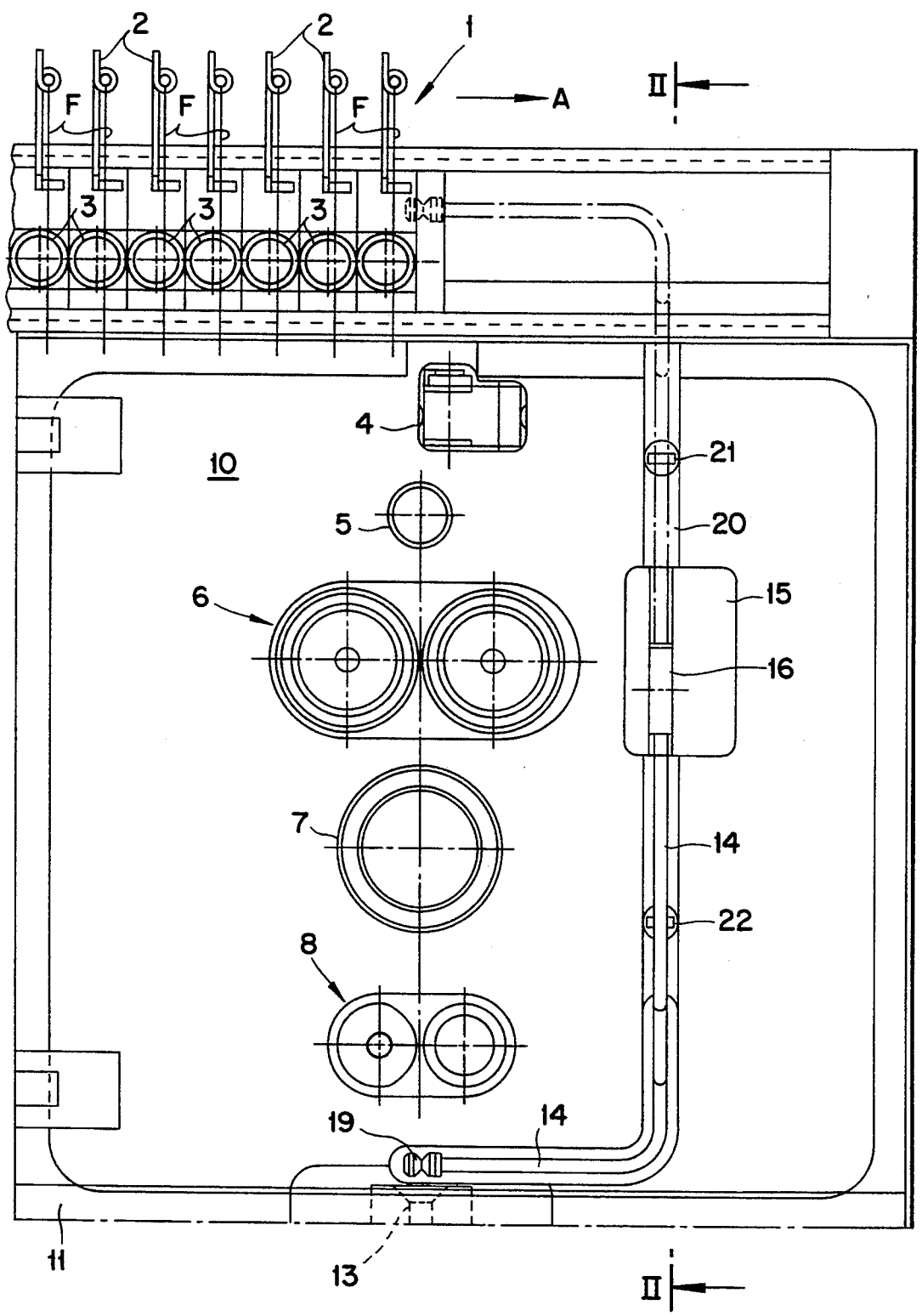
FIG. 1 is a front view in cutout form of a part of a tearing-strength test apparatus containing an insertion mechanism according to the invention.

FIG. 1 shows a front view of the supply part of a tearing-strength test apparatus such as described in EP-A-403,988 and its U.S. counterpart Pat. No. 5,050,437, the disclosures of which are incorporated herein by reference. The thread F to be tested is fed from above to the supply part, runs through this from the top downwards and subsequently passes into the entry portion (not shown) of the actual test part of the test apparatus. As regards the test part, attention is drawn to EP-A-403,988 and its U.S. counterpart Pat. No. 5,050,437.

Figure 2:
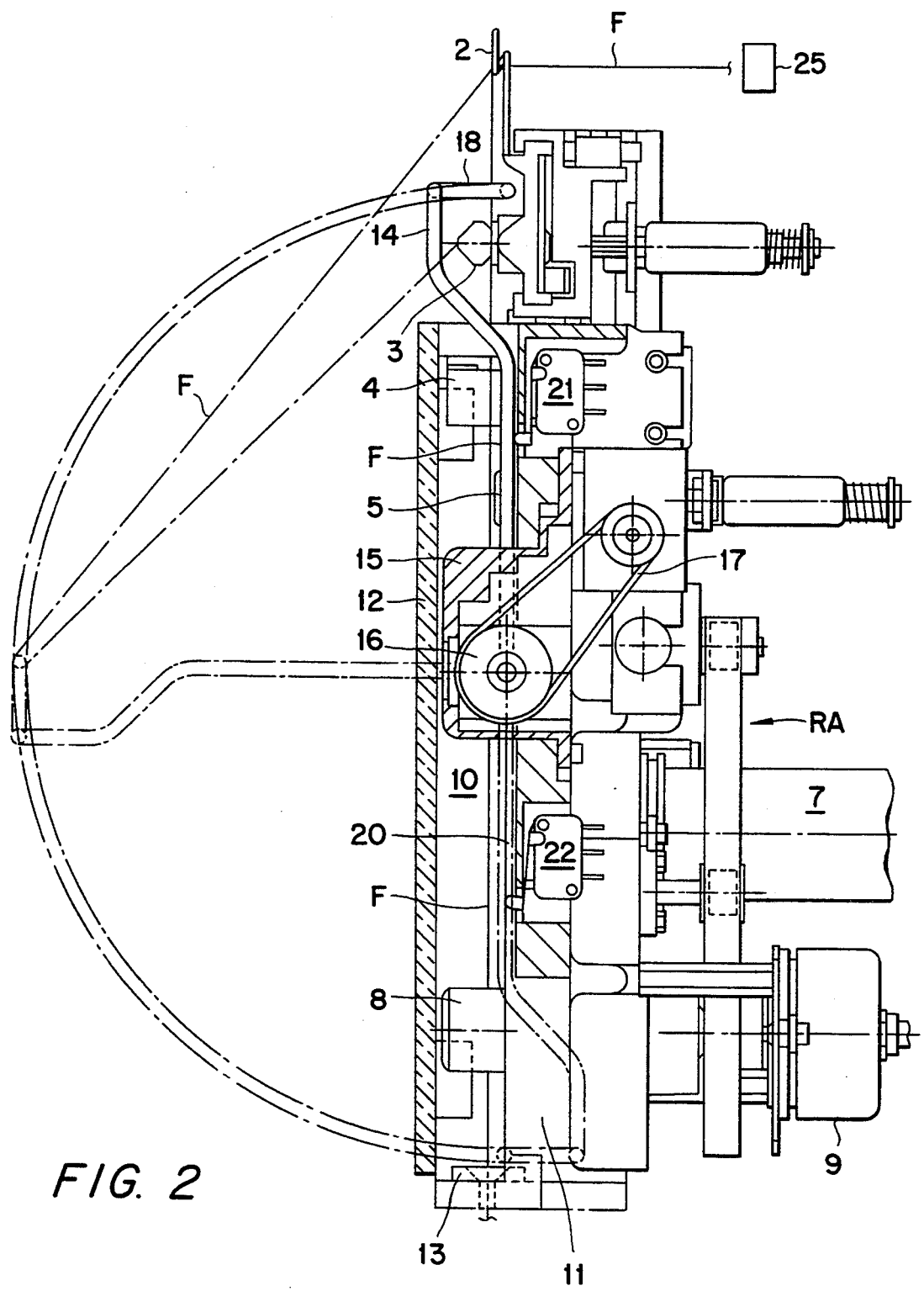
FIG. 2 is a section along the line II—II of FIG. 1.

As illustrated, a yarn changer 1 is arranged at the upper edge of the supply part and consists of thread guide eyes 2 and yarn clamps 3 arranged next to one another. These form a clamping strip displaceable in steps in the direction of the arrow A and having, for example, twelve thread-guide eyes 2 and yarn clamps 3 respectively. Cooperating eye-clamp pairs may be mounted on individual carriers as indicated in FIG. 1, and these can be assembled into the clamping strip shiftable along guideways provided in the apparatus. FIG. 2 generally illustrates a thread supply 25.

The bobbins to be tested are attached on a bobbin store of the type described by way of example in Swiss Patent No. 681,003, and the threads are inserted by hand into the guide eyes 2 and the yarn clamps 3 and clamped between these. As can be taken especially from FIG. 2, the clamped threads can be grasped by a suitable insertion member on their free portion between the thread-guide eye 2 and the yarn clamp 3 and drawn off through the thread-guide eyes 2.

Arranged after the yarn changer 1 in the thread running direction are shears 4, after these a traversing member 5 and downstream of this a pair of motively driveable delivery rollers 6, by means of which the thread F is drawn off continuously from its stock in the test mode. The traversing member 5 is driven to and fro perpendicularly to the drawing plane and at the same time guides the thread F forwards and backwards between the delivery rollers 6, thereby guaranteeing a uniform stress on the delivery rollers 6 and consequently a perfect thread draw-off.

Since the steps of clamping, stretching, tearing and releasing of the thread occur discontinuously in the test part of the tearing-strength test apparatus, but the thread F is drawn off continuously by the delivery rollers 6, a thread store is provided between the delivery rollers 6 and the test part. The thread store comprises a pneumatic thread store 7, such as is known, for example, from air-jet looms. A controlled thread clamp 8 downstream from the thread store 7 consists of a continuously driven control roller with a stepped circumference and of a freely rotatable counter-roller. The controlled thread clamp 8 allows a controlled emptying of the thread store 7, the thread F being either clamped or released by the thread clamp 8 according to the stepped circumference of the control roller.

The drive of the control roller is coupled to that of the delivery rollers 6 via a belt drive RA. An incremental transmitter for the control roller of the thread clamp 8 is designated by the reference symbol 9. As can also be taken from FIG. 2, the members comprising the shears 4, traversing member 5, delivery rollers 6, thread store 7 and controlled thread clamp 8 are arranged in a flat housing which is formed by a milled out stepped portion 10 of a plate 11 and which is closed off at the front by a transparent pivoting door 12. The thread store 7 extends rearwards from the bottom of this stepped portion, and the other members mentioned project above the bottom and reach right up to the pivoting door 12. A suction nozzle 13 is inserted into the side wall of the stepped portion 10 which is located at its bottom in FIGS. 1 and 2. The longitudinal axis of the nozzle 13 is in line with the thread F and the nozzle serves for conveying the thread F out of the thread store 7 into a thread-guide channel of the test part of the test apparatus.

At the beginning of a test, the respective thread F is inserted into the supply part and at the same time brought up to the nozzle 13, by which it is then conveyed pneumatically into the test part. The insertion takes place by means of a mechanism which consists essentially of two components, namely of the yarn changer 1 already described and of an insertion arm 14. The latter is made needle-shaped and has an approximately L-shaped form with a longer leg and with a shorter leg offset from the latter. The longer leg is fastened to a disc-like or block-like carrier 16 which is mounted in a bearing pedestal 15 and which can be driven motively via a toothed belt 17 (FIG. 2). The shorter leg carries at its free end a finger 18, to which a thread guide 19 is fastened. The longer leg extends in the thread running direction and the shorter leg transversely to this.

Figure 3:
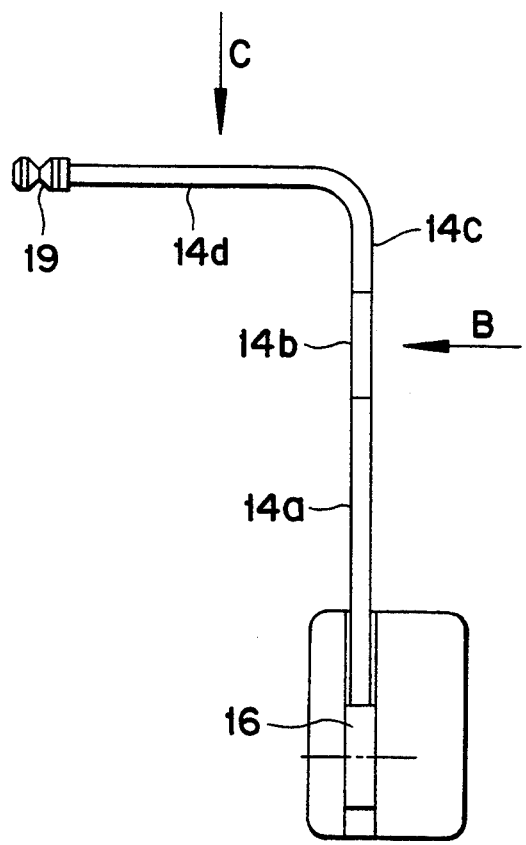
FIG. 3 is a detailed view of the insertion arm shown in FIG. 1, along with its carrier.
Figure 4:
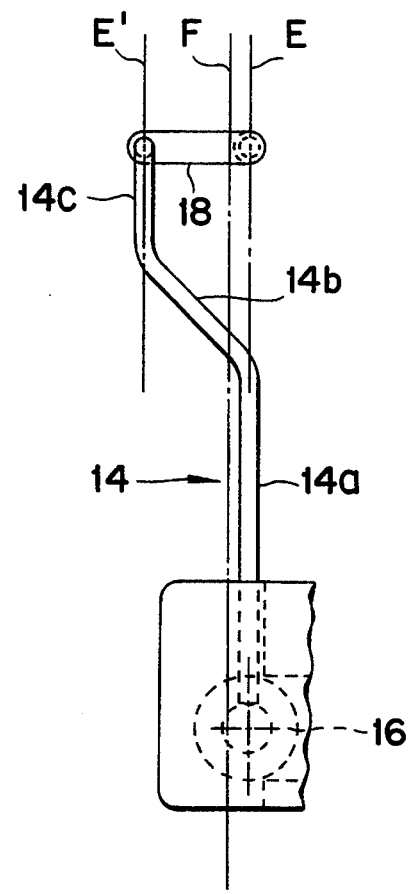
FIG. 4 is a side view of the insertion arm of FIG. 3 looking in the direction of the arrow B in FIG. 3.
Figure 5:
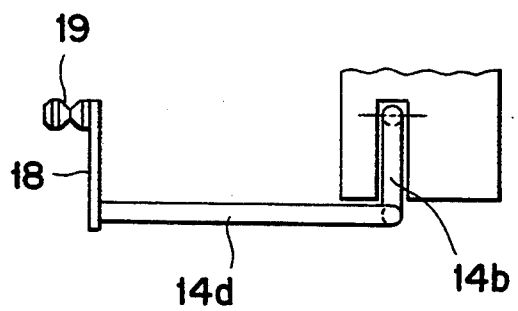
FIG. 5 is a top view of this insertion arm looking in the direction of the arrow C in FIG. 3.

The configuration of the insertion arm 14 and its relation to a desired thread line F (FIG. 4) passing directly between the clamp 3 and the take-over nozzle 13 is shown in FIGS. 3-5.

The longer leg of the insertion arm 14 comprises three portions. A first portion 14a is fastened to the disc-like carrier 16 and extends parallel to the line F between the yarn clamp 3 and the nozzle 13. The axis of this first portion 14a lies in a plane E which lies (with reference to FIG. 1) behind the thread F. Note that the center of rotation of carrier 16 is also located in plane E. Therefore, when the thread contacting part 19 is behind a vertical line between clamp 3 and nozzle 13 in both the top and bottom position, the movement of the arm 14 between these two positions need not pass through an arc greater than 180°.

The second portion 14b of the insertion arm 14 is bent outwardly, and the third portion 14c is parallel to the first portion 14a and lies in a plane E' which is staggered ahead of plane E and of the thread F.

The shorter leg 14d (i.e., the horizontal portion of the insertion arm 14) is annexed to the said third portion 14c and is also extending in plane E'. The shorter leg 14d carries at its free end a finger 18 extending inwardly and having the thread contacting part 19 fastened thereto. The length of the finger 18 is such that the axis of the thread contacting part 19 lies in plane E. Therefore, in the position of the insertion arm 14 shown in FIGS. 2-5 the horizontal portion 14d of the insertion arm will always be spaced a distance in front of any thread portion fixed between a guide eye 2 and its clamp 3.

FIGS. 1 and 2 show the insertion arm 14 in two respective positions, specifically in the position of rest and in the working position. These positions are at an angular distance of 180° from one another. The insertion arm 14 can be pivoted between these positions by means of its drive. The position of rest in FIG. 1 and the working position in FIG. 2 are represented by unbroken lines. In both positions, the thread guide 19 is located approximately level with the bottom of the stepped portion 10 and therefore behind the thread F. In the working position, the insertion arm 14 projects upwards from the stepped portion 10, and the thread guide 19 is positioned in the yarn changer 1 between the thread-guide eye 2 and the yarn clamp 3. In the position of rest, the thread guide 19 is located just above the suction nozzle 13.

A groove 20 which is milled into the bottom of the stepped portion 10 and surrounds the insertion arm 14 and which has a stepped depth makes it possible for the insertion arm 14 to pivot level with the said bottom. In the region of the part of the longer leg of the insertion arm 14 adjoining the carrier 16, there is arranged in the bottom of the groove 20, on each of the two sides of the carrier 16, a microswitch 21, 22 which projects above this bottom and as a result of the actuation of which the motor driving the carrier 16 via the toothed belt 17 is stopped, and a signal indicating that the working position or position of rest of the insertion arm 14 has been reached is generated.

In the functional state illustrated in FIG. 1, the apparatus is prepared for testing a series of threads F; the threads have been inserted into the yarn changer 1 by hand and the insertion arm 14 is in its position of rest where it has remained since the last insertion operation. The delivery rollers 6 are pivoted somewhat apart from one another, so that a gap is formed between them, and the controlled thread clamp 8 is open.

When a starting button is pressed, the suction nozzle 13 is activated and the insertion arm 14 pivots into its working position (FIG. 2). As the arm 14 reaches its working position, a signal is produced by the microswitch 21. The yarn changer 1 is then displaced one step to the right in the direction of the arrow A, with the result that the thread F of the foremost cell (formed from the thread-guide eye 2 and the yarn clamp 3) of the yarn changer 1 is fed to the thread guide 19. The length of the working step of the yarn changer 1 corresponds to half the distance between the threads clamped in the latter.

When the feed position is reached, this being detected by means of the displacement of the yarn changer 1, the drive motor of the carrier 16 is switched on. The result is that the insertion arm 14 is pivoted out of its working position into the position of rest. At the same time, the thread guide 19 describes the half-circle represented by dot-and-dash lines in FIG. 2 and, immediately after leaving the working position, grasps the thread F fed to it. Since this thread is fixed in the yarn clamp 3, it is drawn out of the thread-guide eye 2 as a loop during the pivoting movement of the insertion arm 14, its portion clamped between the yarn clamp 3 and the thread guide 19 being moved in the manner of a pointer towards the connecting axis between the gap between the delivery rollers 6 and the open nip of the controlled thread clamp 8.

After approximately 170° of the 180° pivot angle has been reached, the loop portion of the thread F is first inserted into the controlled thread clamp 8 and then between the delivery rollers 6, until finally the thread guide 19 passes over the entry orifice of the suction nozzle 13 and the thread F is exposed to the suction of the nozzle. Immediately thereupon, the insertion arm 14 reaches its position of rest, this being signalled by the microswitch 22. As a result, the yarn clamp 3 is opened, and the delivery rollers 6 are started and pivoted relative to one another. The thread F is then drawn off from its stock (bobbin) by the rollers 6 and supplied to the test stage by the suction nozzle 13. The thread store 7 also is activated at the same time.

After the conclusion of a test the duration of which is, for example, set on a service unit forming part of the test apparatus or controlled automatically by the said service unit, the yarn clamp 3 is closed and the yarn changer 1 is displaced one working step in the direction of the arrow A. The delivery rollers 6 are simultaneously pivoted away from one another and stopped. The drive of the controlled yarn clamp 8 is likewise stopped, specifically in such a way that the clamp is opened, and the thread store 7 is likewise switched off. The thread F is then located in the effective range of the shears 4 and is cut off by these. The cut-off thread end is sucked away by the nozzle 13. The apparatus is thus ready for a further test and the insertion arm 14 pivots back into the working position.

Of course, before the insertion arm 14 pivots each time back into the working position, the pivoting door 12 is opened. This remains open until the insertion arm 14 has reached its position of rest again and is then closed automatically. The opening of the door 12 is triggered by the actuation of the starting button and the closing by the microswitch 22.

What is claimed is:

1. In a yard tester in which a thread is tested while running from a thread supply through thread feeding means and to take-away means, a threading mechanism comprising a releasable thread clamp between said supply and said feeding means, and a swingable arm means pivotable about an axis between said clamp and said take-away means so that a portion of said arm means remote from said axis contacts a thread portion between said thread supply and said clamp and, upon swinging of said arm means about said axis, draws a loop of the thread to said take-away means.

2. The invention according to claim 1 wherein said thread feeding means includes at least one pair of opposed feed rollers for gripping a thread passing therebetween, wherein said clamp and said take-away means are aligned with said feed rollers, and wherein said arm means brings said loop portion of the thread between said feed rollers during said swinging movement.

3. A method of sequentially threading a plurality of yarns to be tested into test apparatus of the type in which a yarn to be tested is fed from a yarn supply through yarn feed rollers to an air nozzle, said method comprising
  (a) disposing yarn end portions in generally parallel relation to one another with the yarns leading from one of a plurality of guides arranged in a row to one of a plurality of clamps arranged in a row that is generally parallel to said row of guides;
  (b) pivoting about an axis generally parallel to said rows an insertion arm having a yarn engaging member at its end portion that swings, upon pivoting of said arm, from a first position to a second position to contact a portion of a first of said yarns between its guide and its clamp to draw off a loop of said first yarn, to thread said loop between said feed rollers, and to present said loop to said nozzle;
  (c) shifting said rows of guides and clamps endwise after completion of the testing of said first yarn to bring a second of said yarns into alignment with said yarn engaging member on said insertion arm; and
  (d) again pivoting said insertion arm about said axis to draw off a loop of said second yarn, to thread the loop of the second yarn between said feed rollers, and to present the loop of the second yarn to said nozzle.

4. A method according to claim 3, including unclamping said first yarn after the presentation of the loop of the first yarn to said nozzle; severing said first yarn upstream of said rollers after completion of the testing of said first yarn and removing a cut-off end of the first yarn through said nozzle; unclamping said second yarn after the presentation of the loop of the second yarn to said nozzle; severing said second yarn upstream of said rollers after completion of the testing of said second yarn and removing a cut-off end of the second yarn through said nozzle.

5. A mechanism for inserting a thread into a yarn tester of the type having a test stage and a take-over member for the inserted thread, comprising at least one clamp for clamping a portion of the thread and an insertion arm mounted at a fixed location for pivoting movement about an axis between said clamp and said take-over member, said insertion arm including contacting means for contacting the thread upstream of the portion clamped in said clamp and for presenting to said take-over member, upon pivoting of said insertion arm, a loop of said thread having one leg thereof fixed in said clamp.

6. A mechanism according to claim 5, including at least one thread guide arranged in front of said clamp in the thread running direction, and wherein said contacting means contacts a portion of the thread between the thread guide and the clamp.

7. A mechanism according to claim 6, including displaceable carrier means and a plurality of clamps and thread guides carried by said carrier means to form a displaceable clamping strip.

8. A mechanism according to claim 5, wherein said take-over member is an air suction nozzle having an entry orifice for receiving a portion of the thread loop presented by said contacting means.

9. A mechanism according to claim 8, wherein said insertion arm is L-shaped and has two legs, wherein one end of the legs of said insertion arm is fastened to a driveable carrier, and wherein the contacting means includes a thread guide that is located near an end of the other leg of the insertion arm.

10. A mechanism according to claim 9, wherein the leg of the insertion arm fastened to the driveable carrier is oriented parallel to a connecting axis between the clamp and the nozzle, the other leg of the insertion arm is oriented at right angles to the leg that is fastened to the driveable carrier, and the path of the insertion arm during its pivoting movement from the clamp to the nozzle amounts to approximately 180°.

11. A mechanism according to claim 10, including switches actuable by said insertion arm for detecting when respective end positions of the pivoting movement are reached.

12. A mechanism according to claim 11 including a mounting plate for said nozzle and said driveable carrier, displaceable carrier strip means also on said mounting plate and a plurality of clamps and a plurality of thread guides carried by said carrier strip means to form a displaceable clamping strip, respective ones of said thread guides being arranged in front of respective clamps in the thread running direction.

13. A mechanism according to claim 12, wherein said mounting plate is provided with a recess having a groove for receiving the insertion arm, and wherein said mechanism includes a pivotable door for closing off a top of said recess.

14. A mechanism according to claim 13, including a finger disposed between the thread guide and the other leg of the insertion arm, and wherein after insertion of the thread, said insertion arm is positioned in a position of rest with the thread guide in the region of said nozzle.

15. A mechanism according to claim 14, wherein the plurality of clamps are arranged in a row and the plurality of thread guides are arranged in a row that is generally parallel to the row of clamps, and wherein when the mechanism is put into operation, the insertion arm pivots out of the position of rest into a working position where its thread is disposed in the region of the clamping strip, the clamping strip is correspondingly displaced for feeding the thread to be inserted to the insertion arm and the nozzle is activated.

16. A mechanism according to claim 15, wherein the axis about which the insertion arm pivots is generally parallel to said rows of clamps and thread guides, and wherein, after the feed of the thread, the insertion arm pivots out of the working position into the position of rest, and the thread is released from the clamp.

* * * * *